United States Patent
Maity et al.

(10) Patent No.: US 8,363,224 B2
(45) Date of Patent: Jan. 29, 2013

(54) FRINGE LOCKING SUBSYSTEM AND METHODS OF MAKING AND USING THE SAME

(75) Inventors: Sandip Maity, Bangalore (IN); Sameer Dinkar Vartak, Bangalore (IN); Umakant Damodar Rapol, Pune (IN)

(73) Assignee: General Electric Company, Niskayuna, NY (US)

( * ) Notice: Subject to any disclaimer, the term of this patent is extended or adjusted under 35 U.S.C. 154(b) by 490 days.

(21) Appl. No.: 12/751,476

(22) Filed: Mar. 31, 2010

(65) Prior Publication Data
US 2011/0242542 A1   Oct. 6, 2011

(51) Int. Cl.
*G01B 9/02* (2006.01)
(52) U.S. Cl. .................................. 356/450; 356/519
(58) Field of Classification Search .............. 356/450, 356/454, 480, 506, 519
See application file for complete search history.

(56) References Cited

U.S. PATENT DOCUMENTS

| | | | | |
|---|---|---|---|---|
| 3,535,024 A | * | 10/1970 | Schindler | 359/224.1 |
| 3,632,214 A | * | 1/1972 | Chang et al. | 356/457 |
| 7,316,899 B2 | | 1/2008 | McDevitt et al. | |
| 7,491,552 B2 | | 2/2009 | McDevitt et al. | |
| 7,609,376 B2 | | 10/2009 | Wang et al. | |
| 2002/0041611 A1 | * | 4/2002 | May | 372/29.02 |

* cited by examiner

*Primary Examiner* — Hwa Lee
(74) *Attorney, Agent, or Firm* — Jenifer E. Haeckl

(57) ABSTRACT

A fringe locking subsystem for an optical sensing cavity is provided. The subsystem comprises one or more photo detectors that detect a reference signal and a cavity signal; a first amplifier that generates a calculated differential between the reference signal and the cavity signal; a lock-in amplifier that generates a modulation signal based on the calculated differential; and a controller that adjusts a distance within the cavity based on the modulation signal.

19 Claims, 9 Drawing Sheets

FRINGE LOCKING SUBSYSTEM AND METHODS OF MAKING AND USING THE SAME

BACKGROUND

The invention relates to optical detection, and more particularly to optical detection systems and methods using interferometric detection.

Diagnostic tests based on a binding event between members of an analyte-ligand binding pair are widely used in medical, veterinary, agricultural, manufacturing and research applications. Typically, such methods are used to detect the presence or amount of an analyte in a sample, and/or the rate of binding of the analyte to the ligand. Examples of analyte-ligand pairs include complementary strands of nucleic acids, antigen-antibody pairs, and ligand-ligand binding agent, where the analyte can be either a member of the pair, the ligand molecule, or the opposite member.

Diagnostics methods of this type often employ a solid surface on which ligand molecules are immobilized, to which sample analyte molecules bind with high specificity and varied affinities at a defined detection zone. In this type of assay, known as a solid-phase assay, the solid surface is exposed to the sample under conditions that promote analyte binding to immobilized ligand molecules. The binding event can be detected directly, e.g. by a change in the mass, reflectivity, thickness, color or other characteristics indicative of a binding event. Where the analyte is pre-labeled, e.g., with a chromophore, or fluorescent or radiolabel, the binding event is detectable by the presence and/or amount of detectable label at the detection zone. Alternatively, the analyte can be labeled after it is bound at the detection zone, e.g., with a secondary, fluorescent-labeled ligand antibody.

Application of interferometry, for example, as an optical sensor, is challenging when it is being used in an industrial environment due to the high amount of perturbations in industrial environments. For example, in an interferometric measurement, it is desirable for the optical components to be in a vibration free and temperature stabilized environment. The cavity length is critical, because interferometric fringes require a stable optical path to create stable fringes. In some cases, the laser wavelength may shift over the length of the exposure. Although short exposure times (few seconds or less) may reduce the amount of wavelength shift, short exposure times may not always yield desirable results. For example, in the case of holography, short exposure times may not suit the type of holography that is desired.

Typically, transmission loss, reflection loss, or fringe shift is calculated for these types of sensors to account for environmental perturbations (such as vibrations, and temperature changes). When a monochromatic radiation source is employed, then transmission loss, reflection loss, or fringe shift is calculated. However, in the case of a broadband source, it is additionally required to track the spacing of the different wavelengths.

The sensitivity of the sensor depends on the precision with which the changes (transmission loss, reflection loss, or fringe shift) can be tracked. The precision or sensitivity may depend on the optical or electronic noise in the system.

Ideally, it would be desirable to stop everything on the benchtop from resonating, creeping, shrinking, distorting, buckling, flowing, rocking, sinking, expanding, bowing, settling, slipping or waving in the breeze (such as fan breeze). However, this is rarely possible.

Therefore, it is desirable to have an improved optical sensing device with stable path length regardless of the environmental perturbations.

BRIEF DESCRIPTION

In one embodiment, a fringe locking subsystem for an optical sensing cavity is provided. The subsystem comprises one or more photo detectors that detect a reference signal and a cavity signal; a first amplifier that generates a calculated differential between the reference signal and the cavity signal; a lock-in amplifier that generates a modulation signal based on the calculated differential; and a controller that adjusts a distance within the cavity based on the modulation signal.

In another embodiment, a fringe locking subsystem for an optical sensing cavity is provided. The subsystem comprises one or more photo detectors that detect a reference signal and a cavity signal; a first amplifier that generates a calculated differential between the reference signal and the cavity signal; a lock-in amplifier that generates a modulation signal based on the calculated differential; a controller that produces an output in response to the modulation signal; and a driver in at least intermittent communication with the controller, wherein the driver adjusts a distance within the cavity based on the output from the controller.

In yet another embodiment, a method of actively stabilizing a cavity length is provided. The method comprises collecting a reference signal representative of the input light in a cavity and a cavity signal representative of the output light from the cavity; calculating a differential between the reference signal and the cavity signal; converting a phase and amplitude of the differential signal to a time-varying low-frequency-voltage signal to generate an error signal; providing an error signal to a driver to modulate the cavity length; and adjusting a distance between cavity surfaces based on the error signal.

DRAWINGS

These and other features, aspects, and advantages of the invention will become better understood when the following detailed description is read with reference to the accompanying drawings in which like characters represent like parts throughout the drawings, wherein.

DETAILED DESCRIPTION

Figure 1:
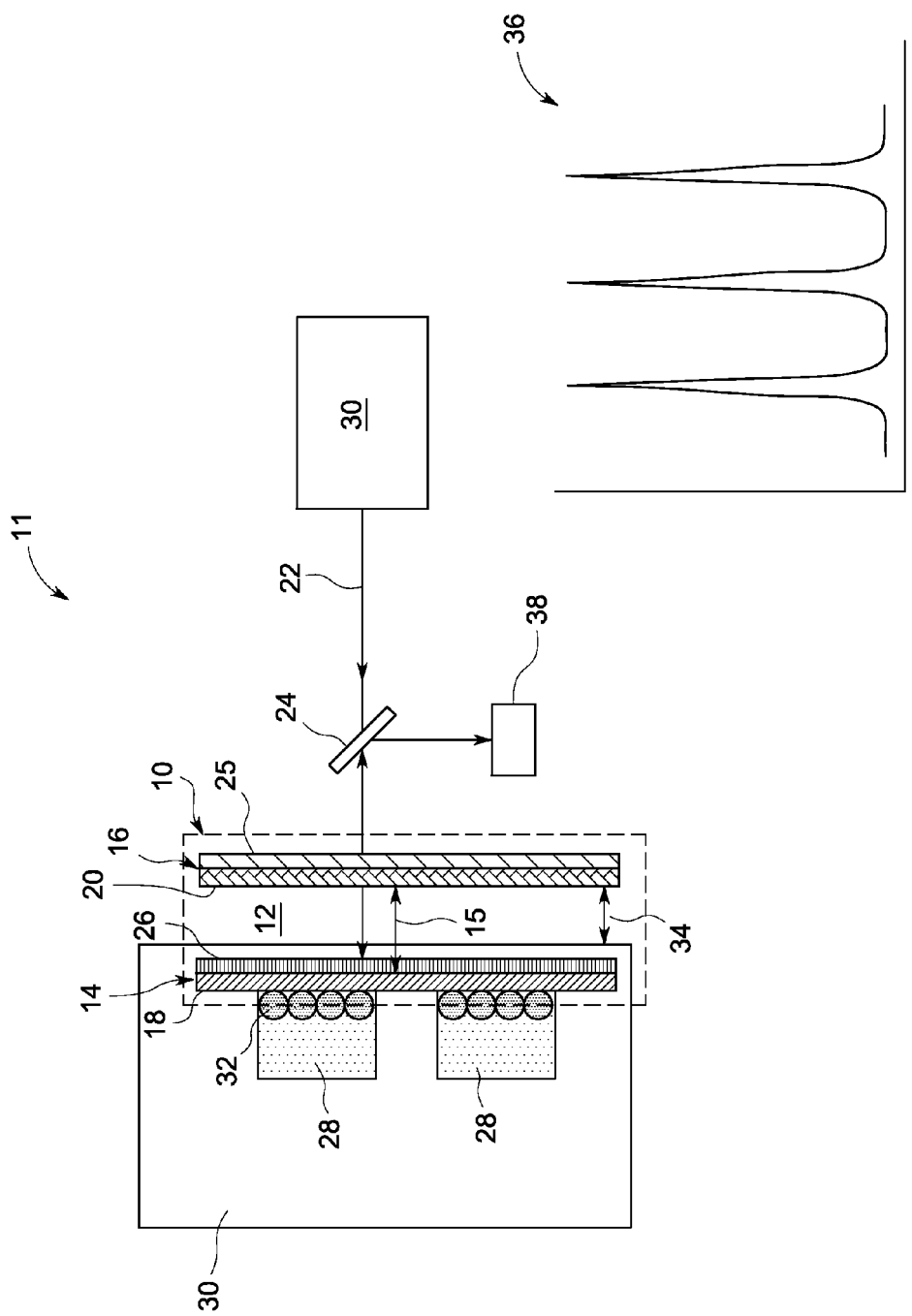
FIG. 1 is a schematic diagram of an optical sensor assembly comprising an embodiment of an optical sensing device of the invention for analyte detection.

In certain embodiments, an optical sensing device is used to detect a concentration of one or more analytes, such as biomolecules, or a rate of association and/or dissociation of one or more analytes in an analyte solution. The optical sensing device comprises a cavity defined by an anomalous reflective element having an anomalous reflection surface, and a non-absorptive element having a non-absorptive reflection surface. The non-absorptive reflection surface is disposed in a direction away from the anomalous reflection surface. In one embodiment, the non-absorptive reflection surface has the ability to reflect back 90 percent or more of the light incident upon the non-absorptive reflection surface. The anomalous reflection surface may be in operative association with a flow cell that contains an analyte solution in fluidic channels.

In certain embodiments, a multi-analyte array format is provided for simultaneous detection of concentration of two or more different analytes in a solution, or a concentration of a single analyte from two or more different analyte solutions. The multi-analyte format can also be used to detect the rate of reaction of the analytes in the solution.

In certain embodiments, the methods of the invention, for detection of analytes, rely upon a change in intensity (as opposed to spectral measurement) of the outgoing light from the cavity, hence, the sensitivity of measurements of the invention is not limited by the resolution of the detector. In one example, the sensitivity of the measurements may be higher than in the case of spectral measurements. In one example, the sensitivity of the optical sensing device is greater than or equal to about 0.1 pg/mm$^2$. In addition, the optical sensing device provides a low cost, portable solution for affinity-based biosensor applications. Also, the optic device enables detection or monitoring of dynamics, such as kinetics of binding and multi-spot sensing.

To more clearly and concisely describe the subject matter of the claimed invention, the following definitions are provided for specific terms, which are used in the following description and the appended claims. Throughout the specification, use of specific terms should be considered as non-limiting examples.

As used herein, the meaning of the term "concentration" of an analyte in a sample solution includes instances in which the sample does not contain any analyte (zero amount) to instances in which the sample contain up to any infinite amount of the analyte in the solution. For example, if the sample solution does not include any of the analyte, the "concentration" of the analyte in the solution will be zero (0).

As used herein, the term "anomalous reflection" refers to a phenomenon when the reflectivity of a surface, such as a gold surface, decreases in the presence of blue or violet light.

As used herein, the term "Fabry-Perot cavity" refers to a structure having at least partially reflecting surfaces that are aligned parallel to each other, the reflections of the light waves between the two surfaces interfere constructively and destructively, to produce a standing wave pattern between the two surfaces.

As used herein, the term "immobilized" includes, but is not be limited to, attached, coated, or deposited.

As used herein, the term "broadband light source" refers to a light source that emits a continuous spectrum output over a range of wavelengths at any given point of time.

As used herein, the term "lock-in amplifier" refers to a type of amplifier that can extract a signal with a known carrier wave from extremely noisy environment (S/N may be 60 dB or less).

In certain embodiments, the optical sensing device functions on the principles of affinity sensor. Light is directed from a light source to the cavity and the absorbance of the light is detected. In certain embodiments, the cavity may be a Fabry-Perot cavity. The anomalous reflection surface and the non-absorptive reflection surface may be disposed parallel to each other. In some embodiments, the light may be directed in the cavity by free space transmission. In these embodiments, the light source is appropriately aligned with the cavity such that the desired amount of light is directed to the cavity. In other embodiments, the light may be transmitted using an optical fiber. In these embodiments, same fiber may be used to direct light to the cavity, and to collect the outgoing light from the cavity.

The light beam, such as the laser beam or the LED beam reflects back and forth within the cavity to cause interference. This back and forth reflection of the light within the cavity enhances the reflections from the anomalous reflection surface and the non-absorptive reflection surface by several times. The separation between the two reflection surfaces, that is the anomalous reflection surface and the non-absorptive reflection surface, and the reflectance or the transmittance of the two surfaces effect the performance of the cavity.

An interference pattern is formed due to multiple reflections of light between the two reflection surfaces. A certain portion of the light incident on the anomalous reflection surface is absorbed by the surface. The amount of absorption of the incident light depends upon the amount of ligand and/or analytes present on the anomalous reflection surface. For example, a ray of light incident at a certain angle in the cavity, enters the cavity with a certain intensity ($I_0$), the next ray reflected twice (once from both the surfaces) has a intensity $I_1$ that is lower than the intensity of the incident ray, and so on.

The varying transmission function of the cavity is caused by interference between the multiple reflections of light between the two reflection surfaces. Constructive interference occurs if the transmitted beams are in phase, which corresponds to a high-transmission peak in the spectrum of the outgoing light from the cavity. If the transmitted beams are out-of-phase, destructive interference occurs which corresponds to a transmission minimum. Whether the multiple-reflected beams are in-phase or not, depends on the wavelength ($\lambda$) of the light (in vacuum), the angle the light travels through the cavity ($\theta$), the length of the cavity (l), and the refractive index of the material between the two reflection surfaces (n).

Further, the intensity of the reflected beam depends on the absorptivity of the surfaces of the cavity. Modifying the absorptivity or reflectivity of the anomalous reflection surface changes both contrast and resolution of the interference fringes. Functionalizing the anomalous reflection surface so that the biomolecules/analytes are adsorbed results in a change in the resolution of the fringes.

The analyte detection by the sensing device is based on a change in the reflection properties (such as intensity) of the anomalous reflection surface for an incident light in a certain wavelength range. For wavelengths of light greater than 550 nm, the anomalous reflection surface behaves as a metal, whereas for blue and purple light having a wavelength in a range from about 300 nm to about 550 nm, the anomalous reflection surface behaves as a dielectric surface rather than a metal. In this case when the anomalous reflection surface behaves as a dielectric surface, multiple reflections in the dielectric layer results in a substantial or at least detectable decrease in the reflectivity. Hence, when a light in a wavelength range from about 300 nm to about 550 nm is incident on an anomalous reflection surface, the anomalous reflection surface absorbs majority of the light, and reflects back only a portion of the incident light. In one embodiment, the anomalous reflection surface has a reflectivity of less than about 50 percent. In addition, when the anomalous reflection surface acts as an affinity sensor, certain chemical or biological species (ligands and/or analytes) may be present on the anomalous reflection surface. The presence of these species results in further decreases in the reflectivity of the anomalous reflection surface.

In one embodiment, the anomalous reflection surface comprises noble metals, such as but not limited to gold, silver, platinum, and alloys thereof, dielectric materials, such as but not limited to, magnesium fluoride, zinc oxide, magnesium sulphide, titanium di-oxide, halfnium dioxide, or combinations thereof. The dielectric materials may be disposed in the form of a single layer or multiple layers. The multiple layers may be stacked together; the stack so formed may be used as the anomalous reflection surface. In one example, the anomalous reflection surface comprises a gold layer. In another embodiment, the anomalous reflection surface comprises a plurality of nanoparticles of the same or different materials. For example, the anomalous reflection surface may comprise a combination of gold and silver nanoparticles.

The analyte may be a biological or a chemical material. For the anomalous reflection surface to act as an affinity sensor for detecting analytes, the anomalous reflection surface is functionalized using ligand molecules. The ligand molecules may be present in the form of a coating, also referred to as functionalized coating. The detection is based on the competitive binding of the analyte to the binding sites of the ligand. The presence of ligands or analyte-binding molecules on the anomalous reflection surface further decreases the already low reflectivity of the anomalous reflection surface. In addition, the reflectivity of the anomalous reflection surface decreases further with the binding of the analytes to the ligands. The reflectivity of the anomalous reflection surface decreases with the increase in the amount of analytes binding to the surface of the anomalous reflection surface. Advantageously, this decrease in reflection is more pronounced due to the anomalous reflection phenomenon, and aids in increasing the sensitivity of the optical sensor. For example, for a 2.5 percent change in reflectance at 470 nm incident excitation wavelength, the resolution of the cavity fringes change by more than 7 percent and the contrast changes by more than 10 percent. Accordingly, the greater the change in reflectance, so to will be a greater change in the resolution and contrast. In one example, a four-fold improvement in sensitivity can be achieved by detecting a change in cavity peak height (contrast).

In certain embodiments, the ligands may be immobilized on the anomalous reflection surface in the form of a layer or a coating. The ligands may be disposed in discrete areas to form an array of discrete analyte-binding regions. In one embodiment, the discrete regions may be used to detect multiple analytes. The detection system may further employ a plurality of flow cells. Each flow cell comprises at least one fluidic channel. Each of the fluidic channels may be aligned to a particular area of the ligand. The ligands may comprise one or more of a biopolymer, an antigen, antibody, nucleic acids and hormone ligands. The ligands may be disposed in a continuous or a discontinuous fashion on the anomalous reflection surface, such as a gold layer. In one example, for antibody binding affinity measurements, an antigen typically is immobilized on the anomalous reflection surface. The anomalous reflection surface is then exposed to a solution containing the antibody of interest, and binding proceeds.

In embodiments relating to multi-analyte detection, the ligands may be disposed in discrete regions, such that one or more of the discrete regions comprises a different ligand molecule than the other regions. In one embodiment, all the different discrete regions may comprise different ligand molecules. In this embodiment, the different discrete regions may be aligned with at least one fluidic channel. In one embodiment, each of the fluidic channels may have a different analyte solution. In this embodiment, a fluidic channel may be aligned with a discrete region having a corresponding ligand molecule. In another embodiment, where multiple analytes are required to be detected in the analyte solution, the different discrete regions may be assigned to detect one of the multiple analytes.

In certain embodiments, the ligand utilizes biologically active reagents such as, for example, antibodies for detecting a specific substance such as, for example, antigens. The marking of the complementarily associated binding partners such as, for example, protein targets or the target nucleic acid, by means of electrically conductive particles is performed according to the known methods such as, for example, the final marking with marked oligonucleotides, by utilizing ligases. In certain embodiments, conventional (bio) molecular binding pairs can be utilized as capturing molecules and as target molecules.

In certain embodiments, the anomalous reflection surface immobilized with ligands may saturate due to high concentrations of the analytes, or due to exposure of the anomalous reflection surface to the analyte solution for a long period time. In these embodiments, the anomalous reflection surface with ligands needs to be regenerated to further detect the analytes. In one example, the regeneration of the anomalous reflection surface may be achieved by applying a different solution than previously used. In one example, the anomalous reflection surface may be exposed to a base solution, such as sodium hydroxide, or to an acidic solution, such as, glycine hydrogen chloride buffer having pH 2.0, to regenerate the anomalous reflection surface. The regeneration of the ligands considerably reduces the cost of the sensor assembly. In one embodiment, regeneration of the ligands enables detection of different analyte solutions. In this embodiment, the ligands are regenerated after detecting an analyte solution, and before flowing the next analyte solution in the fluidic channels.

FIG. 1 illustrates an optical sensing device 10 employed in a sensor assembly 11 for detection of biomolecules (analytes). The sensing device 10 comprises a cavity 12 defined by an anomalous reflective element 14 and a non-absorptive element 16. In one embodiment, the cavity is a Fabry Perot cavity. The cavity 12 may be filled with air, or glass, or a combination thereof.

The anomalous reflective element 14 has an anomalous reflection surface 18, and the non-absorptive element 16 has a non-absorptive reflection surface 20 deposited in a direction away from the anomalous reflection surface. In one example, the anomalous reflection surface 18 comprises a gold layer. In one embodiment, a thickness of the anomalous reflection surface 18 is in a range from about 40 nm to about 60 nm. In one embodiment, the thickness of the anomalous reflection surface 18 is about 50 nm. The cavity length 15 is defined as the distance between the anomalous reflection surface 18 and the non-absorptive reflection surface 20. The cavity length 15 is chosen based upon the wavelength of the light incident on the cavity. In addition, the cavity length 15 depends on the coherence length of the light source. The cavity length 15 is typically smaller than the coherence length of the light source so that the interference is relatively stronger. In one embodiment, the cavity length 15 is in a range from about 3 mm to about 10 mm. The shorter cavity length is mechanically more stable. Hence, it is desirable to have shorter cavity length to reduce any noise produced due to the perturbations in the length of the cavity. The cavity 12 and/or the fluidic chip 32 may be operatively coupled to a temperature controller (not shown).

The system 10 may employ additional optics, such as but not limited to, a collimator, focusing lens, or mirror (not shown). For example, a focusing lens may be disposed at the exit or at a distance from the exit of the cavity to collect all the outgoing light from the cavity 12. The collected light may be focused on to a mirror and reflected in a fiber, to be directed to the detector.

The sensor assembly 11 further comprises a light source 30 for transmitting light in the cavity 12. The light incident in the cavity 12 is reflected between the anomalous reflection surface 18 and the non-absorptive reflection surface 20. The light source 30 emits light in a wavelength range from about 300 nm to about 550 nm to enable the anomalous reflection surface 18 to exhibit anomalous reflection phenomenon. The light from the light source 30 may be monochromatic or a broadband light. The monochromatic light would be appropriately used in cases where the cavity length 15 can be modulated, while the broadband light would appropriately be used in cases where the cavity length 15 is fixed.

Reference numeral 22 represents a beam of light travelling from the light source 30, such as a monochromatic light source or a broadband light source, to the cavity 12. The beam 22 is split into two portions using a beam splitter 24. In one example, the beam-splitter 24 may include a 2×2 fiber coupler or a free-space beam-splitter.

The non-absorptive reflection surface 20 is disposed on a substrate 25. The anomalous reflection surface 18 is disposed at least partially on a transmissive substrate 26. Suitable materials for the transmissive substrate 26 may be materials that have a transmission coefficient in a range from about 50 percent to about 60 percent for a light having a wavelength in a range from about 300 nm to about 550 nm. In addition, the refractive index of the transmissive substrate may be in a range from about 1.331 to about 1.360. Non-limiting examples of the transmissive substrate may include glass, silicon, or quartz. The refractive index of the transmissive substrate 26 is such that most of the light incident upon the transmissive substrate 26 either from the source, or as a result of the reflection from the opposite surface (non-absorptive reflection surface 20), is transmitted through the transmissive substrate 26 and reaches the anomalous reflection surface 18, and there is minimal or no light absorbed by the transmissive substrate 26. In addition, the material of the transmissive substrate 26 is such that a very minimal or zero portion of the light may be reflected back by the transmissive substrate 26. After passing through the transmissive substrate 26, the light is incident upon the anomalous reflection surface 18, a portion of the light incident on the anomalous reflection surface 18 is absorbed by the anomalous reflection surface 18 itself, and the remaining portion is reflected back in the cavity 12. The reflected light travels through the transmissive substrate 26 with minimal or no loss of light in the transmissive substrate 26. The light is then incident upon the non-absorptive reflection surface 20. The light is reflected several times in this manner between the surfaces 18 and 20 before exiting from the cavity 12.

The anomalous reflection surface 18 is, at least in part, in contact with the flow cells 28 of the fluidic chip 30. The anomalous reflection surface 18 is exposed to the analyte solution(s) of the flow cells 28. The ligands immobilized on the anomalous reflection surface 18 may bind with the analytes. As time progresses, more number of analytes bind with the ligands thereby changing the reflectivity of the anomalous reflection surface 18. This change in reflectivity is reflected by a change in the intensity of light in the interference spectrum.

In certain embodiments, the anomalous reflection surface 18 comprises immobilized ligands 32. The type of ligand 32 depends on the type of analyte to be detected. In one embodiment, the ligands or functionalized coating comprises Dextran strands.

The binding of the analytes to the ligands 32 results in at least temporary increase in absorptivity of the anomalous reflection surface 18. The corresponding signals from the cavity 12 reflect the binding events as a dip in the intensity of the reflected light in the interference pattern. After a period of time, if the analyte dissociates from the ligands 32, the dip in the intensity disappears to reflect the dissociation event in the interference pattern. The amount of decrease in the intensity of the reflected light is related to the amount of analytes binding to the ligands 32. Accordingly, the decrease in the intensity of the reflected light is indicative of the concentration/presence of analyte in the analyte solution.

In one embodiment, the non-absorptive reflection surface 20 is made of a non-absorptive reflective ceramic coating. As a way of example, reflective ceramic coating comprises titanium oxide coating. The reflection efficiency of the non-absorptive reflection surface of the non-absorptive element is in a range from about 90 percent to about 99 percent.

In one embodiment, the non-absorptive element 16 scans a portion of the cavity length 15 using an actuator. As illustrated, the non-absorptive element 16 scans a distance ΔL (arrow 34) of the cavity length 15. The cavity length 15 or a portion thereof may be scanned using an acoustic actuator, an electric actuator, magnetic actuator, capacitive actuator, piezoelectric actuator, thermal actuator, or a shape memory alloy based actuator. In one example, a piezoelectric actuator (not shown) may be directly coupled to the non-absorptive element 16.

The optical sensor assembly 11 further comprises a detector 38 that receives outgoing light signal from the cavity 12. In one embodiment, the detector 38 receives spatially spread light signal, for generating a set of discrete electrical signals representing the spatially-spread light signal. The interference spectrum is analyzed by the detector 38 to detect the analytes concentration in the sample. The detector 38 operates to detect a change in the absorption properties of the anomalous reflection surface 18 with the change in the concentration of the analyte binding to the surface of the anomalous reflection surface 18. The amount of protein binding to the anomalous reflection surface 18 governs the absorption of the incident light by the anomalous reflection surface 18.

Graph 36 is an example of an output of the sensing device as a function of the cavity length L (15). The output is in the form of bright and dark fringes as cavity length 15 or wavelength of the incident light is scanned. The height or contrast of the bright and dark fringes, and width or resolution of fringes depend on the mirrors reflectivity (finesse). Finesse is a function of the reflectivity of the cavity surfaces (reflection surfaces 18 and 20), roughness of the cavity surfaces, flatness of the cavity surfaces, and parallelism of the cavity surfaces. In one example, the finesse is a function of the reflectivity of the anomalous reflection surface 18.

The detector 38 may be a photodetector (such as a photodiode), a spectrometer, or a charge-coupled device (CCD), or a camera for measuring reflected light intensity over a selected range of wavelengths. The detector 38 can be a photodetector for recording light intensity. In one example, the photodetector may be a photodiode, such as an avalanche photodiode.

Typically, a photodetector may be employed when using monochromatic light, and the spectrometer, or CCD, or a camera may be employed when using the broadband light. In embodiments where the detector 38 is a charge-coupled detector (CCD) or a camera, the detector 38 may record the spectrum of the reflected light from the sensing device 10. In one embodiment, the spectrometer is a 2-D spectrometer. The 2-D spectrometer may include a 2-D array of suitable resolution. For each of the flow cells 28 in the fluidic chip 30 there is a corresponding column or row in the 2-D spectrometer to measure the interference fringe of the corresponding flow cell of the fluidic chip 30. By quantifying the change in resolution or contrast of the interference fringes, the refractive index changes or molecular interactions in each flow cell 28 can be measured. In another embodiment, the detector 38 is a 1-D spectrometer.

The detector 38 may be coupled to a detection circuitry (not shown). In one example, the detection circuitry may convert current signal to voltage signal. Also, the detection circuitry may amplify the signal received from the detector 38. The detection circuitry may include components, such as but not limited to, data processor, for receiving measurements of interference pattern from the detector 38, such as a spectrometer, and for conducting analysis thereon, wherein the analysis comprises determining a parameter of an interference spectrum. Non-limiting examples of such parameters may include frequency, phase, and intensity of the interference fringes.

In some embodiments, signal to noise ratio (SNR) may be improved by increasing the finesse of the cavity 12. In other embodiment, the SNR may be improved by either integrating or averaging the signal over time. The SNR may also be improved by temperature stabilizing the cavity 12, and/or by fringe locking the cavity 12. Temperature stabilizing, or fringe locking the cavity may reduce or minimize the systematic noise like temperature noise, or mechanical noise.

In certain embodiments, the detector 38 may also include a lock-in amplifier. Lock-in amplifiers may use mixing, through a frequency mixer, to convert the signals phase and amplitude to a DC signal, or time-varying low-frequency voltage signal. Lock-in amplifiers may be used to measure the amplitude and phase of signals buried in noise. The lock-in amplifier acts as a narrow bandpass filter, which removes at least a part of undesired white noise (noise at all frequencies), while allowing through, the signal which is to be measured.

A computer may be used to process and display the signals. The computer may be used to generate a variety of quantitative and qualitative measures. For example, in quantitative measurements, the abscissa may represent time and the ordinate may represent percentage of concentration of an analyte. In addition, the computer may have a spectrum library, which stores the information regarding the spectral characteristics of various elements or chemical compounds. This spectrum library may be used to identify unknown samples by comparing the spectral information received from an unknown sample with spectral patterns retained in the library, and identification of the unknown substance may be made by comparison.

Figure 2:
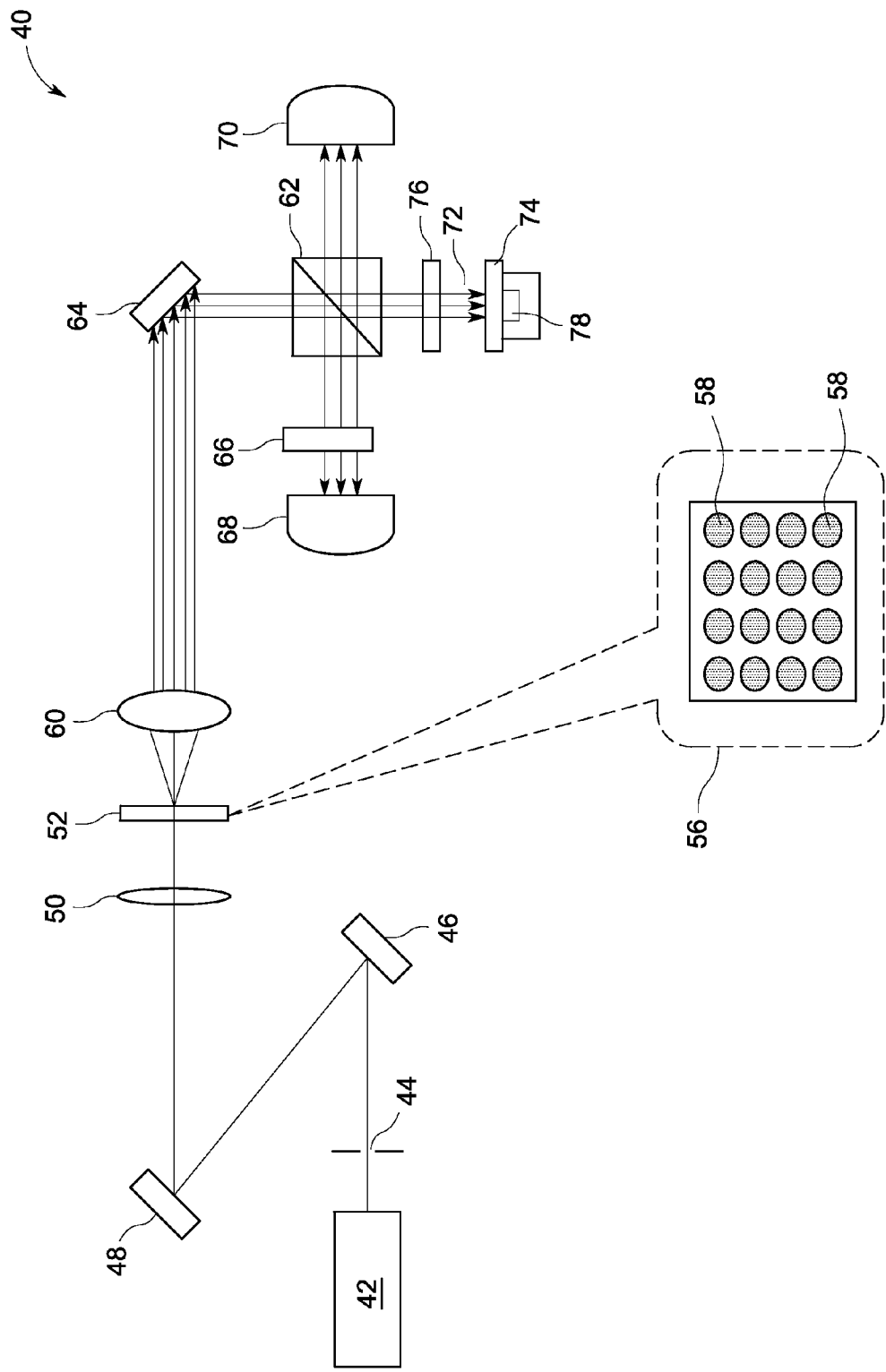
FIG. 2 is a schematic diagram of an embodiment of an optical sensor assembly using multi-spot light patterns for analyte detection.

FIG. 2 illustrates a ray diagram of an optical sensor assembly 40 for multi-analyte detection. The different analytes that need to be detected may be present in a single analyte solution. Alternatively, two or more analyte solutions may be detected for one or more analytes. In the illustrated embodiment, the sensor assembly comprises a light source 42. The light source 42 may be a monochromatic light source or a broadband light source. In one example, the source 42 may be a monochromatic source with a light wavelength of about 470 nm. The assembly 40 also comprises a pinhole 44, and mirrors 46 and 48 for directing light in the direction of the lens 50. In one embodiment, the lens 50 is a convex lens with a focal length of about 100 centimeters. The light from the lens 50 is focused and directed to a multi-spot-generator optic 52. The multi-spot generator optic 52 patterns the light into one or more spatially-spread discrete spots.

As illustrated in the enlarged view represented by dashed rectangle 56, in one example, the multi-spot generator may generate a 4×4 array of spots 58. The array may be a 2×2 array to a 9×9 array. Each of the spots 58 may be identical, or one or more of the spots may be different from the other spots. The spots 58 may vary in size, or shape, or optical properties, such as wavelength of light. In case of broadband light, at least one of the spot 58 may have a different wavelength than the other spots. In one example, the spots 58 may each have a particular monochromatic wavelength. Further each of the spots 58 may either be a 1 dimensional or a 2 dimensional spot.

The patterned light having the array of spots 58 is directed to another lens 60. In one embodiment, the lens 60 is a convex lens. The light is then directed to a beam splitter 62 using a minor 64. In one embodiment, the focal length of the convex lens 62 may be about 50 centimeters. The combination of the two convex lenses 50 and 60 is used to alter the beam size. In one embodiment, the two convex lenses 50 and 60 may reduce the beam size by half.

The beam splitter 62 may comprise diffractive optical elements used to split the light beam into two or more beams. Each of the split beams may have the characteristics of the original beam except for power and angle of propagation. The direction of multiple beams can be organized as either 1-D or 2-D pattern. A neutral density filter 66 is employed to desaturate the detector 68.

A portion of the beam splitted using the beam splitter 62 is directed to the cavity 72. The cavity 72 comprises an anomalous reflective element 74 and a non-absorptive element 76. The anomalous reflective element 72 is in contact with a flow cell 78 having fluidic channels (not shown). The anomalous reflective element may comprise a gold layer as anomalous reflection surface. The non-absorptive element 76 may be a partially silvered aluminum minor. In addition, the non-absorptive element 76 may be piezo-electrically driven to scan a portion of the cavity length.

The two detectors 68 and 70 are used to detect the interference fringes outgoing from the cavity 72. The detector 68 is a reference detector that may track fluctuations in input light intensity which could lead to spurious changes in fringe height or contrast. The detectors 68 and 70 may comprise an array of photodiodes, or a camera. In embodiments where one or both the detectors 68 and 70 comprise an array of photodiodes, photodiodes of the array may be mapped to the corresponding spot 58 of the multi-spot array. The detectors 68 and 70 may be connected to the difference amplifier so that difference between the two detectors 68 and 70 may be amplified to capture the change in the signal from the cavity 72 to reduce or eliminate the undesired effects caused due to fluctuations in the input light.

Figure 3:
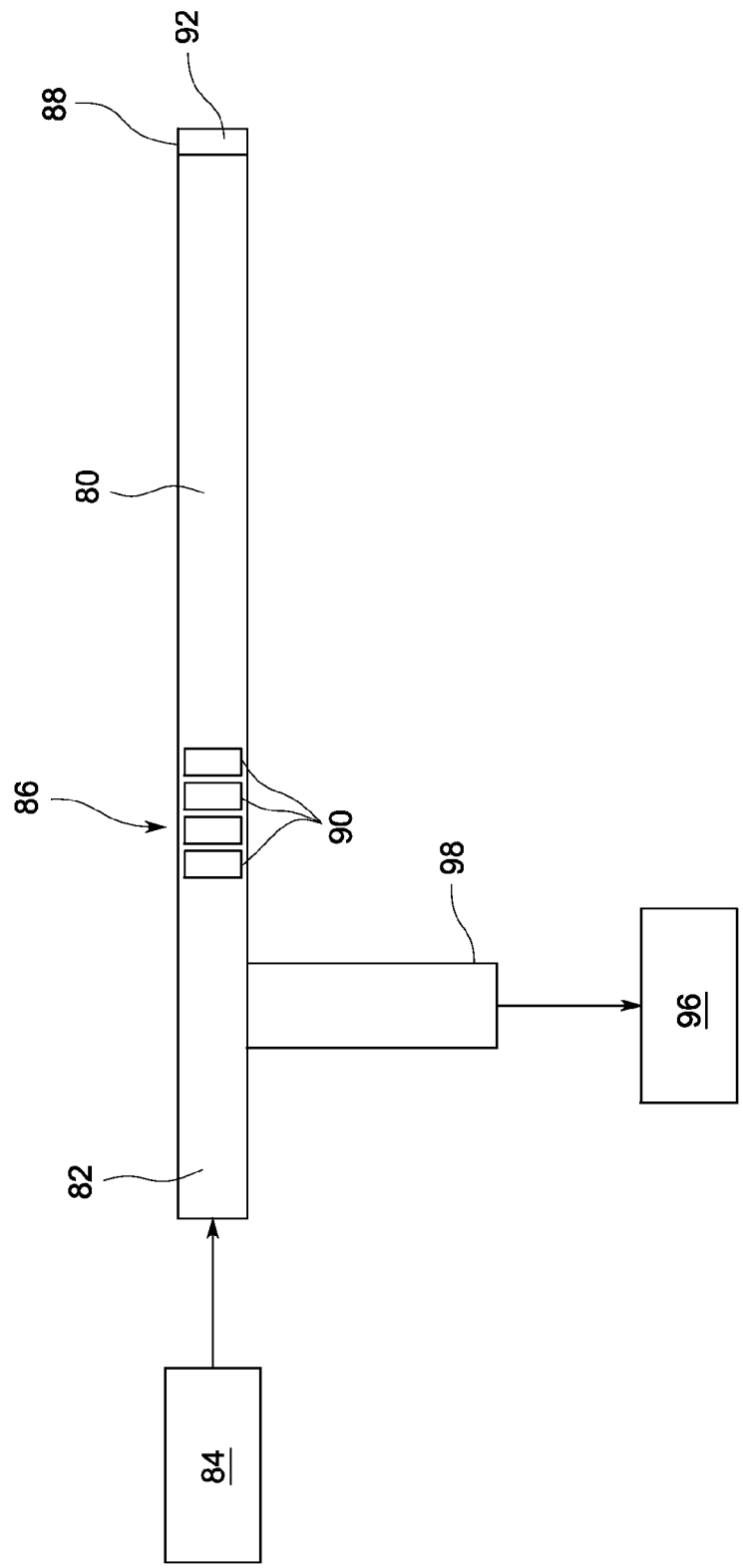
FIG. 3 is a schematic diagram of an embodiment of an optical sensor assembly comprising an optical sensing device disposed in an optical fiber.

FIG. 3 illustrates another embodiment of the sensor where the cavity 80 is disposed in an optical fiber 82. The fiber 82 guides light from the source 84 into the cavity 80. The optical sensor assembly, having the cavity 80 disposed inside the fiber 82, reduces bonding difficulties, is miniature in size, and provides continuous geometry, robust structure and versatile installation. High finesse values can be achieved with a narrow spectral-width fiber Bragg grating 86.

In one embodiment, the fiber 82 is a single mode fiber. The cavity is formed by a non-absorptive element formed of the fiber Bragg Grating 86 and an anomalous reflective element 88. The fiber Bragg grating (FBG) 86 is a type of distributed Bragg reflector constructed in a short segment of an optical fiber that reflects particular wavelengths of light and transmits all others. The fiber Bragg grating 86 includes portions 90 having different refractive index patterns and arranged in a determined fashion. The portions 90 may be disposed in the core of the optical fiber. The portions 90 may be formed by exposing the optical fiber 82 to a pre-designed interference pattern (not shown). The reflection/absorption wavelength of the fiber Bragg grating 86 may be tuned by changing the pitch of the grating portions 90. In one embodiment, the pitch may be tuned by controlling the temperature of the fiber by using a heating element. The fiber Bragg grating 86 causes a periodic perturbation in the optical fiber 82. The fiber Bragg grating 86 may have a submicron size period. The fiber Bragg grating 86 may couple light from the propagating mode to the counter propagating mode at a specific wavelength, which is sensitive to the temperature and strain.

As illustrated, the anomalous reflection surface 92 is disposed at a distal end of the optical fiber 82 in a direction away from the light source 84. The anomalous reflection surface 92 may employ a gold layer.

The optical fiber 82 may also employ a beam splitter 94 in the path of the light such that the beam of light from the light source 84 is split (for example in 1:2 ratio) before reaching the FBG 86. In one embodiment, a portion of the split light beam may enter the cavity 80 and then reflect back and forth between the non-absorptive element 86 and the anomalous reflective element 88. The other portion of the light may be directed towards the detector 96 via the fiber 98 to serve as a reference.

Fiber optic biosensors have advantages over other devices in terms of miniaturization, immunity to electromagnetic interference and resistance to harsh environment. In addition, very small sample volumes, including in-vitro spaces can be detected. Also, by bundling the fibers, highly multiplexed analyses of binding reactions may be carried out. The capability for multiplexing and remote sensing also makes fiber optic sensors superior to other competitors.

Figure 4:
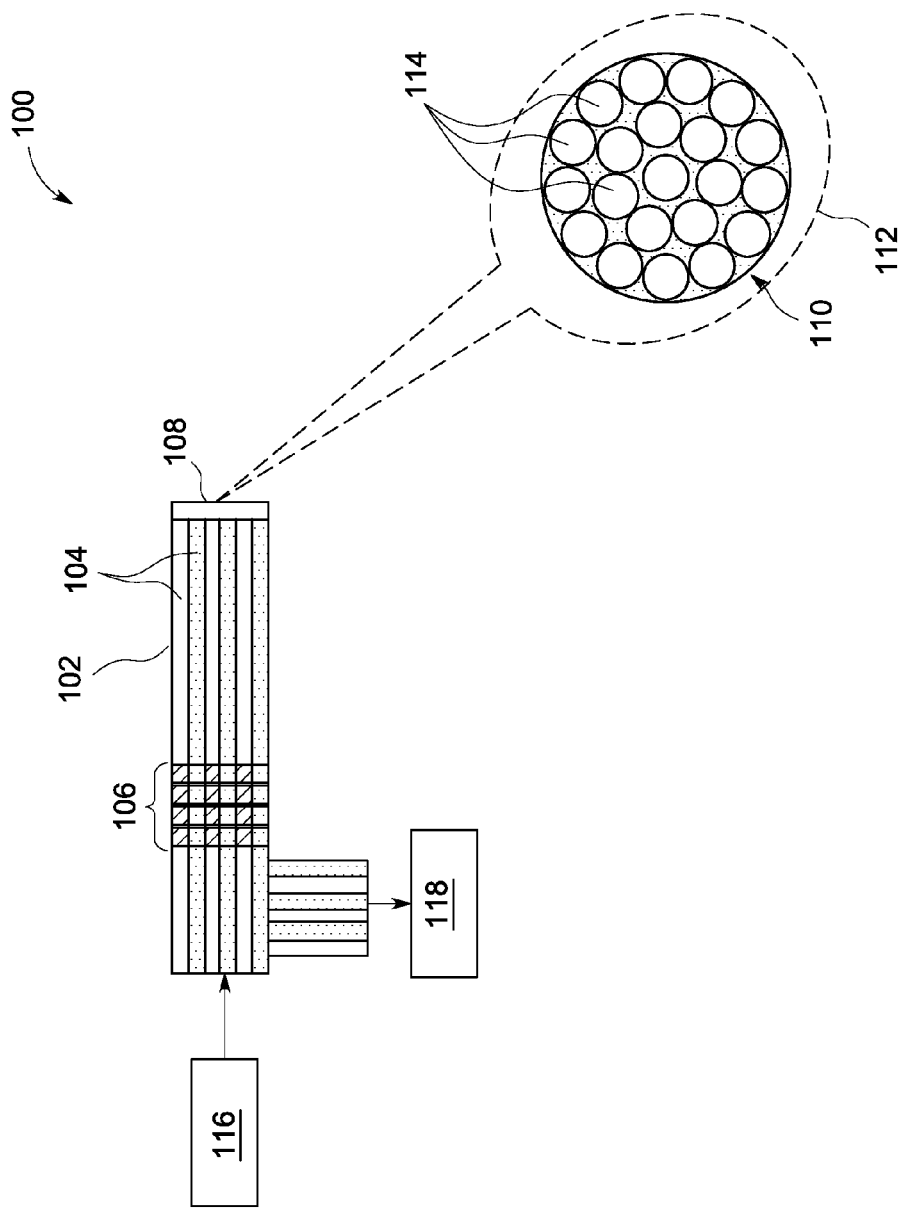
FIG. 4 is a schematic diagram of an embodiment of an optical sensor assembly comprising an optical sensing device disposed in an optical fiber.

FIG. 4 illustrates an embodiment of an optical sensing assembly 100 designed for detecting a plurality of analytes. A fiber bundle 102 comprises an array, such as a circular array 102 made of individual optical fibers 104. The optical assembly 100 comprises the basic elements, such as the fiber Bragg gratings or non-absorptive elements 106, and anomalous reflective elements 108 in an array format. The enlarged view of the cross-section 110 of the fiber bundle 102 from the side of the anomalous reflective elements 108 is shown with a dashed circle 112 surrounding an array of sensing spots 114. Each of the optical fibers 104 in the bundle 102 may employ either the same or different sensing devices. For example, each of the optical fibers 104 in the bundle 102 may employ either the same or different non-absorptive elements 106 and anomalous reflective elements 108. Each of the reflection surfaces may be in operative association with a flow cell (not shown). Each fiber 104 may be aligned with an assay region or a ligand region, such that each fiber is directing a portion of the light from the light source 116, and receiving reflected outgoing light from its aligned detection region. Similarly, the optical coupler (not shown) in the sensor assembly 100 serves to preserve the alignment between the sensing spots 114 and the corresponding positions on the detector 118. In one embodiment, the detector 118 may include a camera, or a two dimensional CCD to capture the plurality of sensing spots 114.

Depending on whether the cavity length is fixed, the method of the invention for optical detection generally, but not necessarily, uses either a monochromatic light that is directed to the cavity and the length of the cavity is varied, or a broadband light that is directed to the cavity while keeping the cavity length fixed. In the latter approach, the change in contrast of the fringes of individual spectral components is monitored due to the change in the reflectivity of the anomalous reflection surface.

Figure 5:
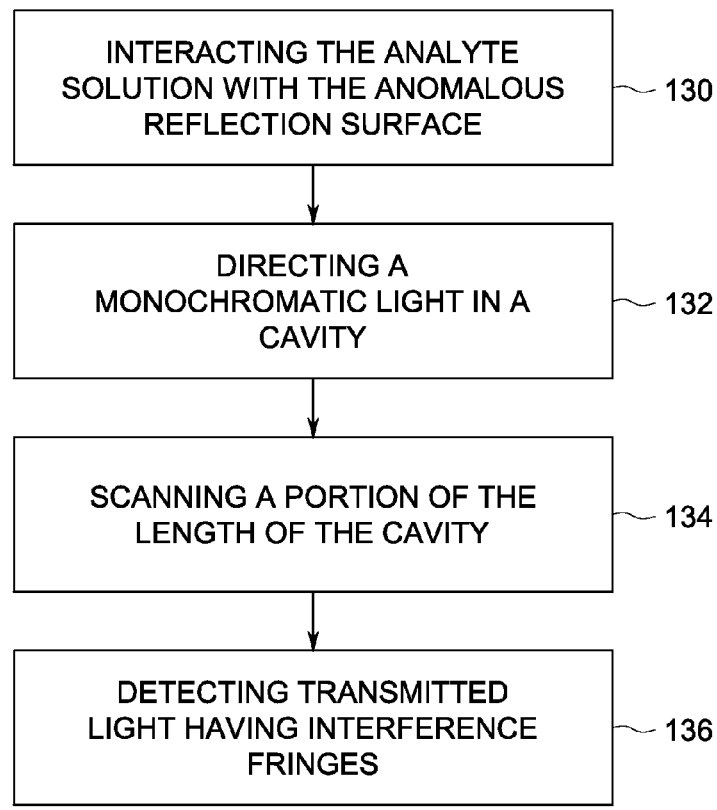
FIG. 5 is a flow diagram of an example of a method of the invention for analyte detection using a monochromatic light.

A method of detecting an analyte using a monochromatic light is illustrated in FIG. 5. At block 130, the method begins by reacting/interacting the analyte solution with the ligand molecules immobilized on the anomalous reflection surface of a cavity. The cavity is defined by the anomalous reflection surface and a non-absorptive reflection surface. The cavity is mounted on an opto-mechanical mount. The reaction between the analyte solution and the anomalous reflection surface having the ligand molecules results in binding of some of the analyte molecules to the ligand molecules. The binding of the analytes to the ligands results in an increase in the absorptivity (and a decrease in the reflectivity) of the anomalous reflection surface.

At block 132, a monochromatic light is directed in a cavity, such as a Fabry-Perot cavity. The cavity may be disposed either inside or outside an optical fiber. The wavelength of the light directed in the cavity is dependent on the cavity length. The wavelength of the monochromatic light may be any wavelength in a range from about 300 nm to 550 nm. The incident light may have a monochromatic wavelength. In one example, the monochromatic light may have a wavelength of about 470 nanometer, and the length of the cavity may be about 10 mm to about 20 mm.

The monochromatic light may be produced using a light source, such as a narrow-band light emitting diode or a laser. The light is reflected multiple times between the anomalous reflection surface and the non-absorptive reflection surface, before exiting the cavity. In certain embodiments, at least a portion of the length of the cavity is scanned to obtain the interference fringes. The non-absorptive element may be used to scan a determined length of the cavity. In one embodiment, the scanning frequency may be in a range from about 3 Hz to about 10 Hz. The scanning length may depend upon the opto-mechanical mount resonance frequency of the cavity. System noise is typically reduced by averaging the data. For systems possessing uncorrelated noises, SNR depends on root of the average of data samples, hence, SNR can also be improved by increasing the scanning duration and data collection frequency.

At block 134, the light transmits through the cavity when the outgoing light resonates with the incident light, that is, when the distance between the two surfaces, the anomalous reflection surface and the non-absorptive reflection surface, is an integral multiple of the wavelength of the light. The transmitted light comprises fringes having maxima and minima, when the distance between the surfaces of the cavity is scanned. A binding event is reflected by a dip in the intensity, and a dissociation event is reflected by a resurfacing of the intensity from the dip. The height or contrast of the fringes, as well as the width of the fringes, depend on the reflectance of the cavity surfaces. Thus, when the biomolecules are present on the anomalous reflection surface the modified reflectance of the anomalous reflection surface causes a greater modification in the fringe width and contrast. This increases modification of the fringe parameters and increases the sensitivity of detection. At block 136, the transmitted light is detected using a fringe detector. When employing a monochromatic light for detection, the transmitted light may be detected using a photodiode.

Figure 6:
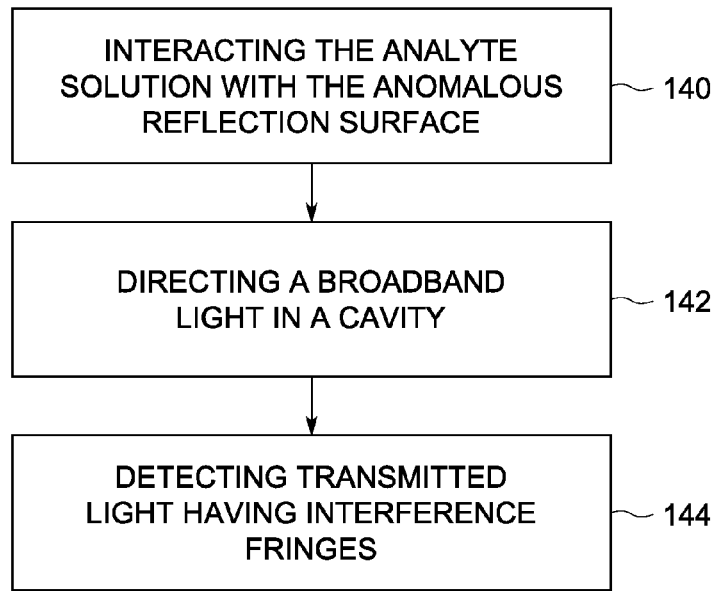
FIG. 6 is a flow diagram of an example of a method of the invention for analyte detection using broadband light.

FIG. 6 illustrates a flow diagram for detecting an analyte using a broadband light, where the broadband light is in a blue/violet region. At block 140, the analyte and functionalized anomalous reflection surface of the cavity are allowed to interact. At block 142, the broadband light is directed in the cavity at a certain angle such that the broadband light is reflected multiple times between the two surfaces, the anomalous reflection surface and the non-absorptive reflection surface, within the cavity. The broadband light comprises two or more wavelengths in a range from about 300 nm to about 550 nm. The light source for the broadband light may comprise a light emitting diode, or a combination of two or more light emitting diodes having a light output of different wavelength. At block 144, the light transmitted out of the cavity is detected for binding/dissociation events or to study the kinetics of reactions. The transmitted light from the cavity comprises interference fringes that are produced due to certain wavelength components of the broadband light being selectively transmitted through the cavity depending on the cavity length.

Light is transmitted through the cavity when it resonates with the incident wavelength, for example, the distance between the two surfaces of the cavity is an integral multiple of the wavelength of the incident light. The transmitted light comprises fringes (e.g. maxima and minima) when either the wavelength of light or the distance between the surfaces is scanned. The height, or contrast of the fringes, as well as their width, depends on the reflectance of the mirrors.

In certain embodiments, the optical sensing device may use a fringe locking subsystem to stabilize the fringes in the cavity and to minimize or eliminate vibration related artifacts from the output of the cavity. The fringe locking subsystem may also be used to minimize the optical noise, and to lock the fringe to reduce the effect of environmental perturbations on the cavity signal. In one embodiment, the fringe locking system may actively stabilize the cavity length.

In one embodiment, system parameters, such as but not limited to cavity length, scan frequency, or scanning speed, may be adjusted to obtain a single fringe in the cavity for scan of the entire cavity length. The system parameters may also be adjusted to obtain a desirable fringe contrast. The desired fringe contrast may be obtained by iteratively setting the cavity length, scan frequency, or scanning speed. In one example, for a determined value of the cavity length, the scan frequency may be adjusted till a desirable fringe contrast is achieved. In one example where a piezo-electric actuator is used to alter/modify the cavity length, a voltage applied to the piezo-electric actuator may be altered to vary the scan frequency or scan speed to enable enhanced fringe contrast. Once the desired fringe contrast is obtained, the cavity may be subjected to fringe locking to obtain peak transmission.

The subsystem may comprise one or more photo-detectors that detect a first signal and a second signal. In one embodiment, the first signal comprises a reference signal, and the second signal comprises a cavity signal. In one embodiment, the first and second signals comprise a unit of amplitude and a unit of time. The subsystem further comprises a first amplifier that generates a calculated differential between the first and second signals, a lock-in amplifier that generates a modulation signal or error signal based on the calculated differential, and a controller that adjusts a distance within the cavity based on the modulation signal. The subsystem further comprises a controller that adjusts a distance within the cavity based on the modulation signal.

In one embodiment, the subsystem may include two photo-detectors, where the first photo-detector detects a reference signal for the light entering the cavity, and the second photo-detector detects a cavity signal or the light outputting from the cavity. In embodiments where a monochromatic light is used in the cavity, the reference detector and/or the cavity signal detector may include a photodiode. In one embodiment, both the reference detector and the cavity signal detector may be photo-diodes. In this embodiment, one photo-diode may act as a reference photodiode and the other photodiode may act as a cavity signal photodiode for measuring a signal from the cavity. In embodiments where a broadband light is used in the cavity, the photo-detector may include a spectrometer, or a camera.

In one embodiment, the reference signal and the cavity signal are provided to the first amplifier, which uses the two signals to generate a calculated differential between the two signals. The calculated differential serves as an input for the lock-in amplifier.

In certain embodiments, the lock-in amplifier may be used to measure the amplitude and phase of signals otherwise difficult to detect due to high amount of noise. In one embodiment, the lock-in amplifier generates a modulation signal based on the calculated differential. In one embodiment, the error signal is a first harmonic signal. In the lock-in amplifier, the calculated differential signal may be further amplified to a level suitable for demodulation at a later stage. The lock-in amplifier may include an input gain stage, a reference circuit, a demodulator, and a low pass filter. The frequency of the signal to be measured, and hence, the band pass region of the low pass filter is set by a reference signal of the lock-in amplifier. The lock-in amplifier reference signal may be supplied to the lock-in amplifier along with the calculated differential signal. The lock-in amplifier reference signal is required to be at the same frequency as the modulation signal. In one embodiment, the lock-in amplifier reference signal comprises a sinusoidal wave function. The sinusoidal function comprises the same frequency as that of the calculated differential signal. The lock-in amplifier reference signal may be phase shifted with respect to the calculated differential signal. The input signal, that is, the calculated differential signal, and the lock-in amplifier reference signal are multiplied together. Multiplication of the two waveforms, that is, calculated differential signal and the lock-in amplifier reference signal, provides the sum and difference frequencies.

As the input signal (calculated differential signal) to be measured and the lock-in amplifier reference signal are of the same frequency, the difference frequency between the two signals is zero. Accordingly, a DC output proportional to the amplitude of the input signal and (the cosine of) the phase difference between the two signals is obtained. In other words, the DC output level from the multiplier is proportional to the input signal. The noise signals may be present at the output of the demodulator and may have amplitudes 1000× larger than the DC offset. As the various noise components on the input signal are at different frequencies to the reference signal, the sum and difference frequencies are non-zero and do not contribute to the DC level of the output signal. This DC level (which is proportional to the input signal) may be recovered by passing the output from the demodulator through a low pass filter. A low pass filter removes majority of the undesired noise while allowing through the signal that is to be measured.

In addition, the subsystem employs a controller that in conjunction with a driver for the non-absorptive element adjusts a cavity length based on the modulation signal received from the lock-in amplifier. The actuator or the driver of the non-absorptive element is responsible for displacement of the non-absorptive element. In one embodiment, the driver is a piezoelectric-driver. The driver may be at least in intermittent communication with the controller. For example, once the cavity reaches its stable state, the driver may be disconnected from the controller. In one embodiment, the controller may be a proportional integrator (PI) controller. In one embodiment, the cavity length may be adjusted by moving the non-absorptive element relative to the anomalous reflective element. The cavity length may be adjusted in one single step by moving the non-absorptive element by the desired distance at once. Alternatively, the cavity length may be changed gradually, by moving the non-absorptive element in a plurality of successive small steps. The movement of the non-absorptive element changes the path length of the light reflecting in the cavity to stabilize the fringe(s).

In certain embodiments, the fringe locking subsystem may comprise a waveform generator in communication with the controller. In these embodiments, the waveform generator and the controller together may be used to adjust the cavity length to compensate for the environmental perturbations. The waveform generator may be employed to provide a waveform function input to an actuator or a driver of the non-absorptive element. The waveform function and the output of the lock-in amplifier may serve as an input for the controller. The combination of the waveform function and the output of the lock-in amplifier together, may be processed by the controller, to provide an output, which, when fed to the driver, accounts for any undesired changes in the cavity length. In one example, where the waveform generator is in communication with the controller, the waveform generator generates a signal that, together with the output of the lock-in amplifier, generates a modulation signal that determines the extent to which the driver adjusts the distance within the cavity. The modified signals may account for environmental perturbations, such as, but not limited to, vibrations and temperature changes.

Figure 7:
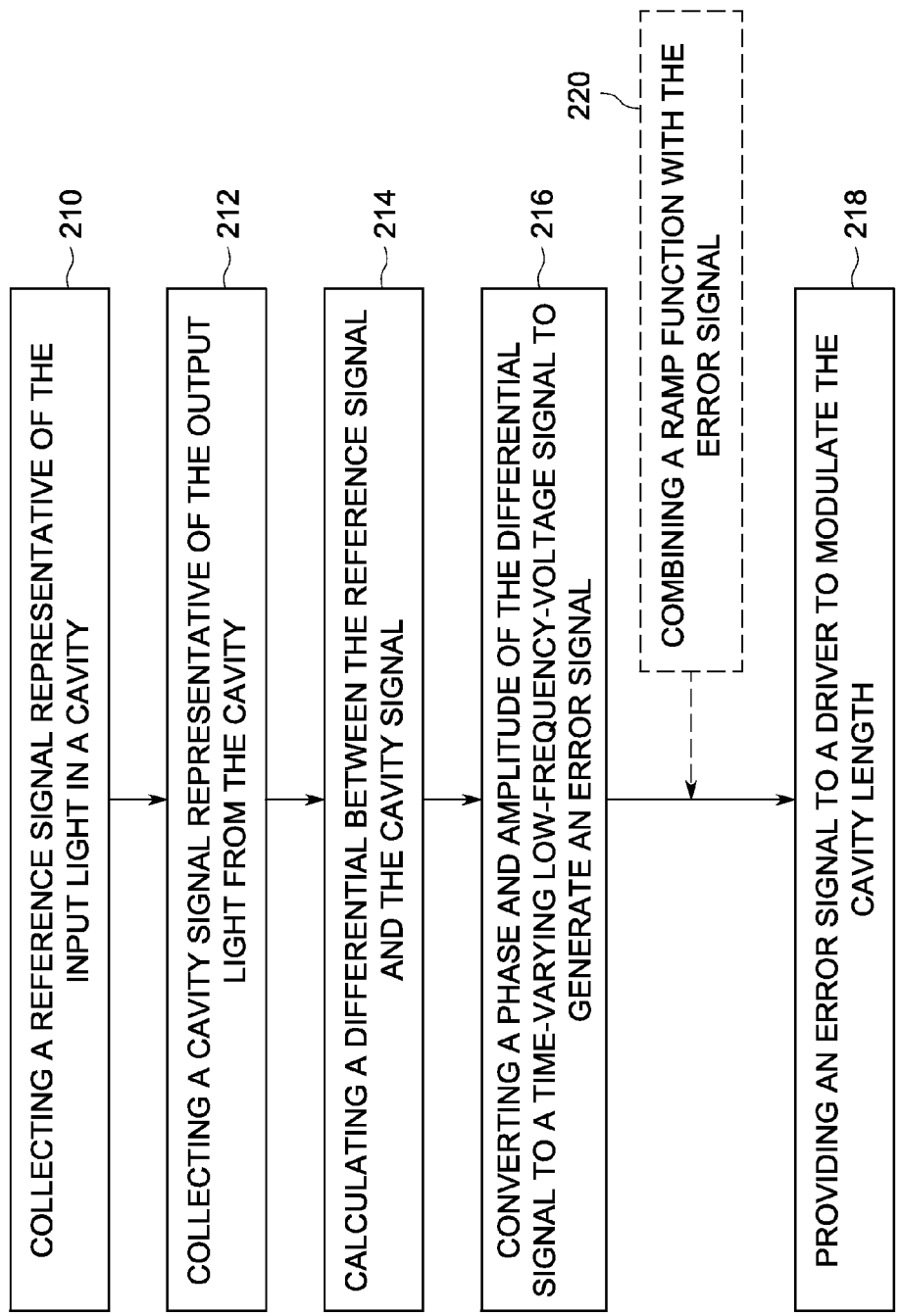
FIG. 7 is a flow chart of an example of a method for fringe locking to actively stabilize a cavity length.

FIG. 7 illustrates a method for actively stabilizing a cavity length. At block 210, the method comprises collecting a reference signal representative of the input light in a cavity. At block 212, a cavity signal representative of the light exiting the cavity is collected. At block 214, a differential is calculated between the reference signal and the cavity signal. In one example, the differential between the signals may be amplified to obtain a calculated differential signal. At block 216, a phase and amplitude of the calculated differential signal is converted to a time-varying low-frequency-voltage signal to generate an error signal. In one example, the error signal is a first harmonic signal. At block 218, a distance between cavity surfaces is adjusted based on the error signal. For example, the error signal is provided to a driver operatively coupled to the non-absorptive element of the cavity to modulate the cavity length. Optionally, at block 220, a ramp function may be combined with the error signal. In one embodiment, the error signal and the ramp function may be proportionally integrated to provide an integrated signal to the driver.

Figure 8:
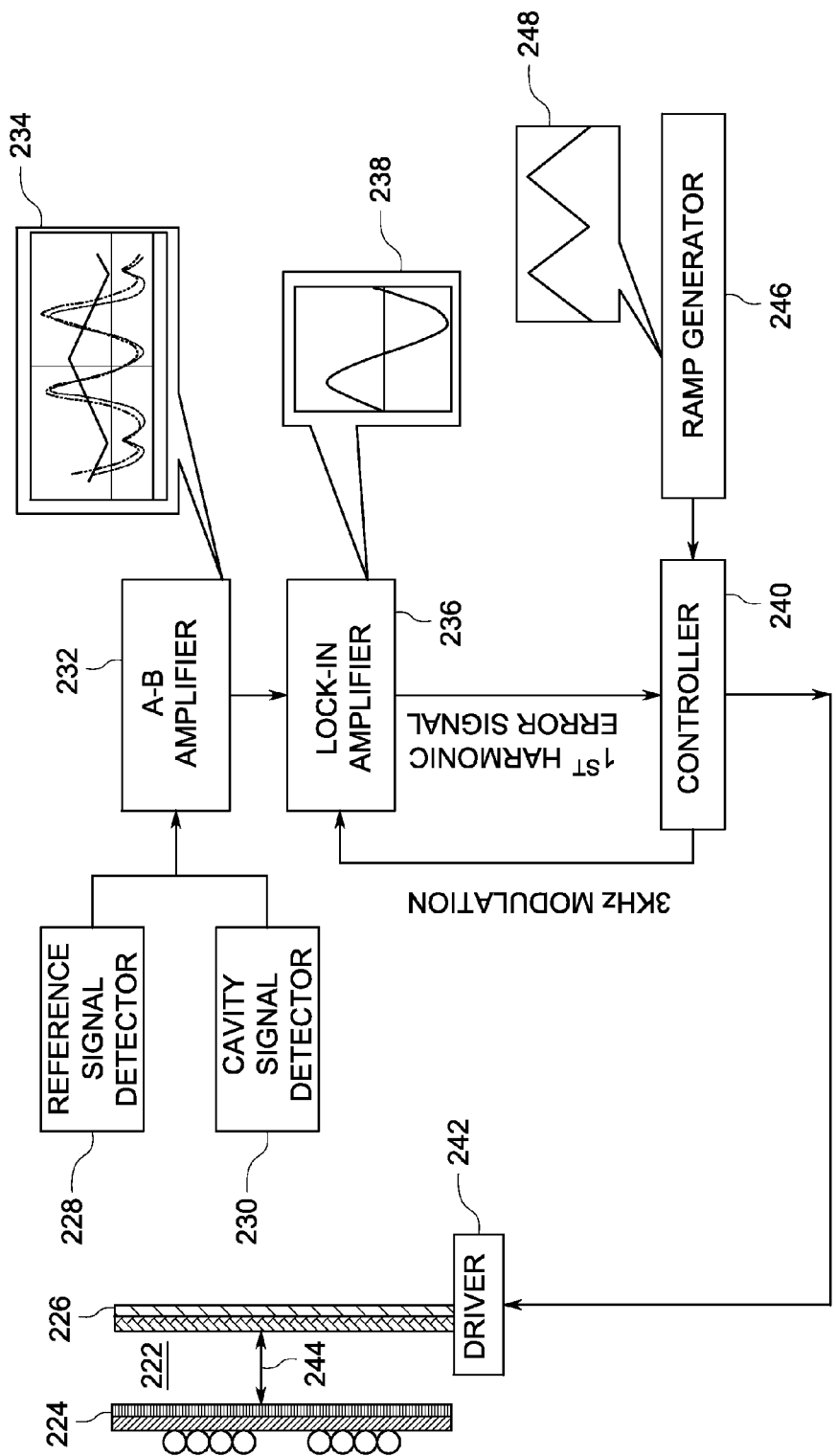
FIG. 8 is a schematic representation of an example of a fringe locking subassembly.

Referring to the schematic illustration of FIG. 8, a cavity 222 is defined by an anomalous reflective element 224 and a non-absorptive element 226. The cavity 222 may receive light from a light source (not shown in FIG. 8). A portion of the light directed towards the cavity 222 may be used as a reference beam. For example, a beam splitter may be used to split the beam of light (before it enters the cavity 222), and a portion of the splitted beam may be directed to a reference signal detector 228. The outgoing beam from the cavity 222 is directed to a photodetector 230. The photodetectors 228 and 230 are in communication with an amplifier 232 to calculate the difference between the photodetectors 228 and 230 as illustrated by graph 234. A lock-in amplifier 236 is used to generate a modulation signal on the order of 3 KHz. In the illustrated example, the lock-in amplifier 236 employs a sinusoidal reference signal 238 to compute the modulation signal. The modulation signal serves as an input for the controller 240. In one example, the lock-in amplifier 236 produces a first order harmonic signal as the modulation signal. In one example, the controller 240 comprises a U3A, an adder that adds offset to the modulation voltage.

A second input to the controller 240 is a ramp function generated by the ramp function generator 246 that is in communication with the controller 240. The reference numeral 248 depicts an example of a ramp function. The output of the controller 240 is fed to the driver 242 to adjust the cavity length 244. The driver is in operative association with the non-absorptive element 226 of the cavity 222. The driver 242 may be connected to the controller 240 using a single pole double thrown switch. Once the cavity length is stabilized, the driver 242 may be disconnected from the controller 240 by changing the mode of the switch to lock mode. Subsequently, if there is any further change in cavity length, the lock mode of the switch may be discontinued and the driver may be again set in communication with the controller 240.

Although discussed primarily with regard to interferometery, the fringe locking technique may also be employed in other fields, such as but not limited to holography. For example, the fringe pattern exhibited at a film upon which the hologram is recorded may be magnified and observed by one or more photo detectors. To compensate for any motion of the fringe pattern detected by the photo detectors, the path length of either a reference beam or an object beam may be adjusted by using the fringe locking subassembly to maintain a stable fringe pattern. For this purpose, a suitable component, for example, one of the mirrors used to direct the object beam or the reference beam, may be mounted on a driver to move the component in a determined direction to a determined distance. The driver may be in intermittent communication with the controller, and so forth. In one example, a voltage signal may be applied to a piezoelectric driver to desirable move the component.

EXAMPLES

Figure 9:
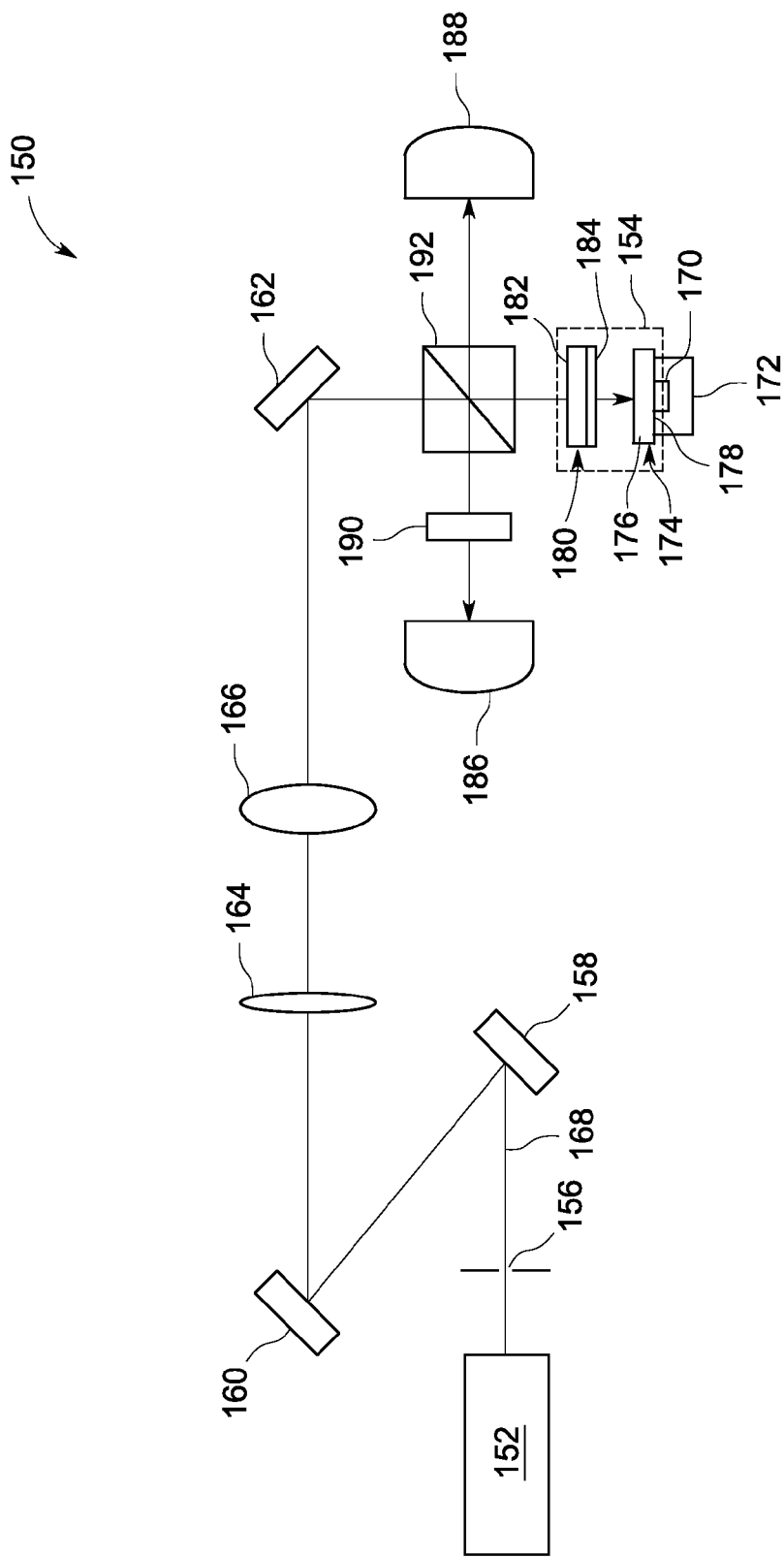
FIG. 9 is a schematic diagram of an embodiment of an optical sensor assembly using monochromatic light for analyte detection.

FIG. 9 illustrates an optical sensing device 150 that focuses at least a portion of the light signal from the light source 152 into the cavity 154. The length of the cavity is about 10 mm. The light source 152 emits light having a wavelength of about 470 nm. A pinhole 156; minors 158, 160 and 162; and lenses 164 and 166 are used to direct and shape the light beam 168 into the cavity 154. Lenses 164 and 166 may be used for beam size reduction to match the width of the fluidic channel (not shown) of the flow cell 170 of the fluidic chip 172. PIN photodiodes 186 and 188 from OSI Optoelectronics are used as the detector. In addition, a neutral density filter 190 and a beam splitter 192 obtained from Thorlabs, USA is also used.

The light source 152 is a 405 nm, 5 mW TM00 mode laser from Power Technology, Inc., USA. The wavelength of the laser 152 is about 405 nm, and the laser power was about 3 mW. The beam size of the laser source 152 is about 1 mm The beam size was reduced to 500 microns by using two convex lenses 164 and 166 of focal lengths 50 mm and 100 mm, respectively. Both the lenses 164 and 166 are obtained from Thorlabs, USA. The beam size is reduced to match the width of the fluidic channel of the flow cell 170. The flow cell 170 is a X-100 flow cell obtained from Biacore, Sweden. The flow cell 170 is formed on a CM5 chip 172, also obtained from Biacore, Sweden. The fluidic channel had a width of about 500 μm and a depth of about 100 μm. The custom made opto-mechanical mount is fixed on the copper base plate. The copper base plate is temperature controlled by a TEC from MELCOR, USA and TEC controller from Wavelength Electronics Inc, USA. The temperature of the copper base plate is maintained at 19° C.

The anomalous reflective element 174 is made of a 500 μm thick glass substrate (transmissive substrate) 176, having one side coated with a gold layer 178. The thickness of the gold layer 178 is 40 nm. The area of the glass substrate 178 and the gold layer 178 is about 10 mm×10 mm. The anomalous reflection surface 178 is in operative association with the CM5 chip 172. The CM5 chip 172 is 10 mm×10 mm in area. The anomalous reflective element 174 is coupled to the CM5 chip 172 by a mechanical mount (not shown). Additional Teflon® rings (not shown) are provided to prevent leaking of the analytes present in the fluidic chip 172.

The non-absorptive element 180 is made from 2 mm thick quartz wafer 182 having a diameter of 25.4 mm Titanium oxide coating (non-absorptive reflection surface) 184 is deposited on one side of the quartz wafer. The thickness of the titanium oxide coating 184 is about 50 nm. The non-absorptive element 180 is mounted with linear stage peizo actuator (not shown) for scanning a portion of the cavity length. The scanning frequency is 5 Hz.

A syringe pump is used to inject the analyte solution in to the flow cell. Sample Flow Rate was 10 micro liter/minute. The sequence used is—Buffer-Protein-Buffer-Analyte-Buffer. Sodium hydroxide (NaOH) is used for regeneration of the immobilized ligand molecules on the anomalous reflection surface. The analyte solution comprised of a protein with pI 5.1 solution in Sodium acetate buffer having a pH of 4.0. The concentration of analyte used was 5 micromolar. Buffer used is HBS-EP having a pH of 7.4. Regeneration solution is 25 μM NaOH solution. A layer of Dextran is used as ligand molecules. Protein is binding electro-statically to Dextran layer. A TDS series oscilloscope from TEKTRONICS, USA is used to visualize the data. The oscilloscope is connected with a National Instrument GPIB card to transfer the data to the computer and Graphical User Interface was written in LabVIEW obtained from National Instruments, to visualize and store the data for further analysis.

For measurements, buffer is passed through the flow channels at a rate of 10 mm/min and the corresponding data is recorded. Peak to peak voltage is measured, and the buffer is passed through the flow channels for 30 minutes to stabilize the flow. Once the flow is stabilized, the analyte solution is passed through the flow channels for 30 minutes. Once the flow is stabilized, the peak-to-peak value of the voltage is recorded and plotted with respect to time. A change in the peak-to-peak to voltage value corresponds to the protein concentration in the analyte solution.

Figure 10:
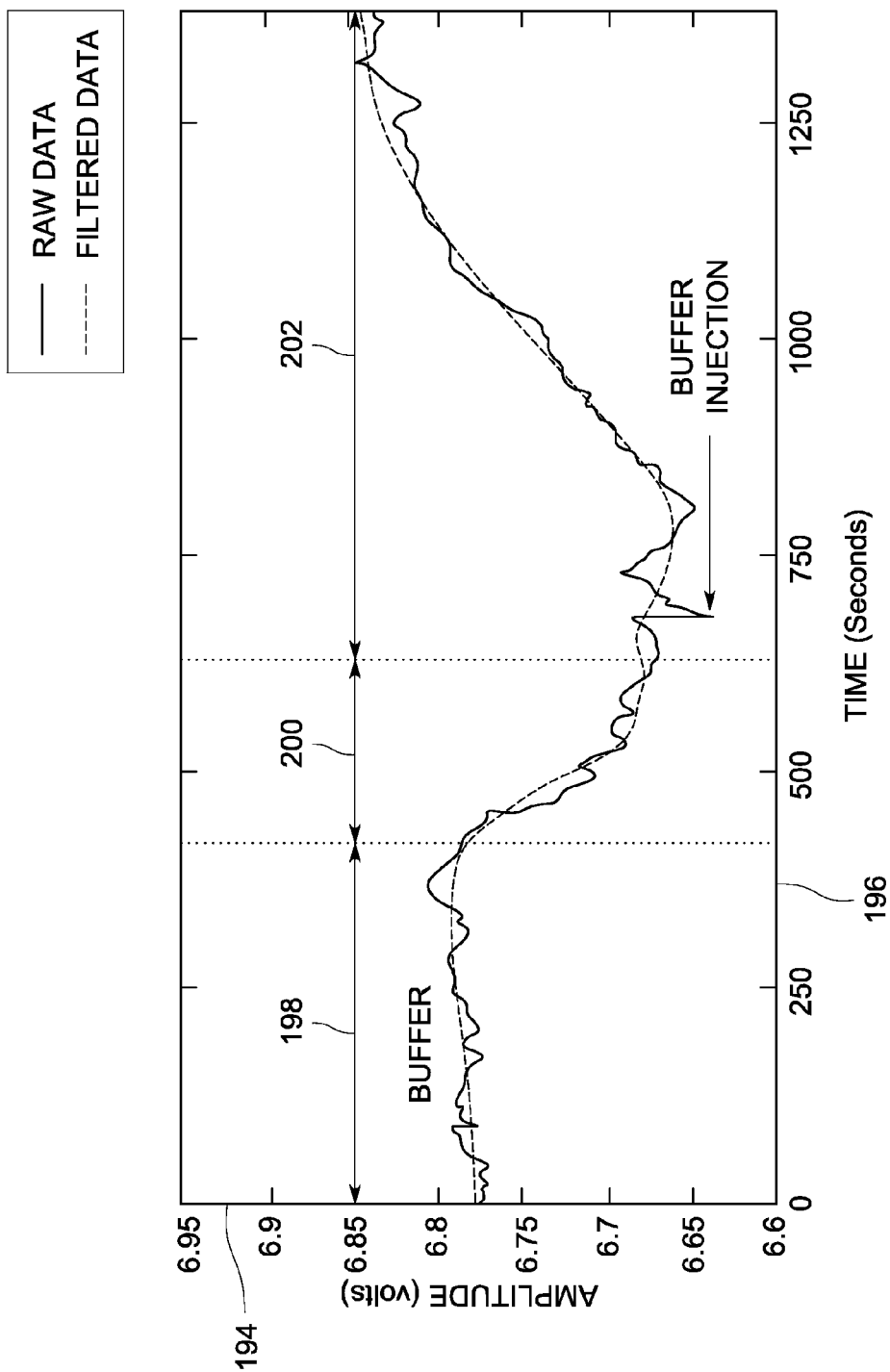
FIG. 10 is a graph of a signal response from cavity based on the fluid in the flow cell.

As illustrated by the graph in FIG. 10, signal (ordinate 194) from the cavity remained virtually constant for the time period 198 when the buffer solution is passed through the flow cell 170. As the solution is passed through the flow cell 170, the signal decreased with time (abscissa 196) during the time period 200. The anomalous reflection surface 178 is regenerated during the time period 202.

The optical sensing device may be used in a variety of applications, for example, in molecular biology and medical diagnostics where specific binding of bioactive molecules to their corresponding binding partners, for example, DNA, proteins, need to be determined. Based on the electrical detection of specific molecular binding events, the affinity sensor may be used to monitor, for example, molecules, viruses, bacteria, and cells in the most diverse samples, such as clinical samples, food samples, and environment samples such as, plants, whereby such monitoring is performed in a time efficient manner. The optical sensing devices may be used in the fields of molecular detection and concentration analysis of biomolecules, kinetic and equilibrium analysis of biochemical reactions, control of fermentation processes, evaluation of ligand-cell-interactions, clinical analysis, and cell demotion. In certain embodiments, the optical sensing device may be used in the molecular biology field, for example, in medical diagnostics, biosensor technology or DNA-microarray technology, for detecting specific molecular binding events.

Advantageously, the monitoring or detection can be performed in real-time. For example, binding reactions may be monitored in real time, thereby reducing cost. The principles and practice of the methods described and claimed may be used to analyze any binding reaction, including, but not limited to, those involving biological molecules. For antibody binding affinity measurements, an antigen typically is immobilized on the sensing surface. That surface then is exposed to a solution containing the antibody of interest, and binding proceeds. Once binding has occurred, the sensing surface is exposed to buffer solution (e.g. one that initially has no free antibody) and the dissociation rate is continuously monitored in real time. One or more embodiments of the sensing device are a low cost and simple optical sensing device. In addition, the devices can be used for multiple-point sensing, thus providing a high throughput.

While only certain features of the invention have been illustrated and described herein, many modifications and changes will occur to those skilled in the art. It is, therefore, to be understood that the appended claims are intended to cover all such modifications and changes as fall within the scope of the invention.

The invention claimed is:

1. A fringe locking subsystem for an optical sensing cavity, comprising:
   one or more photo detectors that detect a reference signal and a cavity signal;
   a first amplifier that generates a calculated differential between the reference signal and the cavity signal;
   a lock-in amplifier that generates a modulation signal based on the calculated differential; and
   a controller that adjusts a distance within the cavity based on the modulation signal.

2. The fringe locking subsystem of claim 1, further comprising a waveform generator in communication with the controller.

3. The fringe locking subsystem of claim 2, wherein the waveform generator generates a signal that together with the modulation signal determines the extent to which the controller adjusts the distance within the cavity.

4. The fringe locking subsystem of claim 1, further comprising a driver in at least intermittent communication with the controller.

5. The fringe locking subsystem of claim 4, wherein the driver is a piezoelectric-driver.

6. The fringe locking subsystem of claim 1, wherein the controller is a proportional integrator.

7. The fringe locking subsystem of claim 1, wherein the first and second reference signals comprise a unit of amplitude and a unit of time.

8. The fringe locking subsystem of claim 1, wherein the first and second photo detectors comprise photodiodes.

9. The fringe locking subsystem of claim 1, wherein the first and second photo detectors comprise spectrometers or cameras.

10. The fringe locking subsystem of claim 1, wherein the error signal is a first harmonic signal.

11. A fringe locking subsystem for an optical sensing cavity, comprising:
    one or more photo detectors that detect a reference signal and a cavity signal;
    a first amplifier that generates a calculated differential between the reference signal and the cavity signal;
    a lock-in amplifier that generates a modulation signal based on the calculated differential;
    a controller that produces an output in response to the modulation signal; and
    a driver in at least intermittent communication with the controller, wherein the driver adjusts a distance within the cavity based on the output from the controller.

12. The fringe locking subsystem of claim 11, wherein the driver comprises one or more of an acoustic actuator, an electric actuator, magnetic actuator, capacitive actuator, piezoelectric actuator, thermal actuator, or a shape memory alloy based actuator.

13. The fringe locking subsystem of claim 11, wherein a frequency of the modulation signal is of the order of 3 KHz.

14. A method of actively stabilizing a cavity length, comprising:
    collecting a reference signal representative of the input light in a cavity and a cavity signal representative of the output light from the cavity;
    calculating a differential between the reference signal and the cavity signal; converting a phase and amplitude of the differential signal to a time-varying low-frequency-voltage signal to generate an error signal;
    providing an error signal to a driver to modulate the cavity length; and
    adjusting a distance between cavity surfaces based on the error signal.

15. The method of claim 14, further comprising amplifying the differential signal.

16. The method of claim 14, further comprising combining a ramp function with the error signal.

17. The method of claim 16, comprising proportionally integrating the error signal and the ramp function to provide an integrated signal.

18. The method of claim 16, wherein the ramp function comprises a sinusoidal wave function.

19. The method of claim 14, wherein the error signal is a first harmonic signal.

* * * * *